(12) United States Patent
Brewer et al.

(10) Patent No.: US 6,263,238 B1
(45) Date of Patent: Jul. 17, 2001

(54) AUTOMATIC EXTERNAL DEFIBRILLATOR HAVING A VENTRICULAR FIBRILLATION DETECTOR

(75) Inventors: James E. Brewer, Cottage Grove; Ann M. Donohoo, Maple Grove; Kenneth F. Olson, Edina, all of MN (US)

(73) Assignee: SurVivaLink Corporation, Minneapolis, MN (US)

( * ) Notice: Subject to any disclaimer, the term of this patent is extended or adjusted under 35 U.S.C. 154(b) by 0 days.

(21) Appl. No.: 09/293,263

(22) Filed: Apr. 16, 1999

Related U.S. Application Data
(60) Provisional application No. 60/082,026, filed on Apr. 16, 1998, and provisional application No. 60/093,950, filed on Jul. 23, 1998.

(51) Int. Cl.[7] ............................................. A61N 1/39
(52) U.S. Cl. ..................................................... 607/5
(58) Field of Search ................................................. 607/5

(56) References Cited

U.S. PATENT DOCUMENTS

| | | | | |
|---|---|---|---|---|
| 4,202,340 | * | 5/1980 | Langer et al. ........................ | 128/419 |
| 4,296,755 | * | 10/1981 | Judell ................................... | 128/705 |
| 4,796,620 | * | 1/1989 | Imran ................................... | 128/706 |
| 4,969,465 | * | 11/1990 | Pless et al. .......................... | 128/419 |

* cited by examiner

*Primary Examiner*—William E. Kamm
(74) *Attorney, Agent, or Firm*—Patterson, Thuente, Skaar & Christensen, P.A.

(57) ABSTRACT

In an automatic external defibrillator (AED) having a ventricular fibrillation detector, the ventricular fibrillation detector may generally be defined as a filter containing both an adaptive non-linear section and a linear section. The non-linear section is preferably a complex-domain neural network that can be trained to differentiate between various rhythm patterns and produce linear data for input to the linear section. The linear section is preferably an ongoing, continuous operation based on a sliding window of a pre-determined time period, e.g., a tapped time-delay filter. In combination the non-linear section and linear section of the filter operate to detect and extract artifacts from a patient's ECG signal in a substantially accurate fashion so that the determination to deliver a defibrillation pulse may be accurately made.

17 Claims, 9 Drawing Sheets

AUTOMATIC EXTERNAL DEFIBRILLATOR HAVING A VENTRICULAR FIBRILLATION DETECTOR

CLAIM TO PRIORITY

This application claims priority to U.S. provisional application No. 60/082,026 filed Apr. 16, 1998, and entitled "Method for Extracting Artifacts in a Single Lead Electrocardiography Systems with Pipelined Neural Networks" and U.S. provisional application No. 60/093,950 filed Jul. 23, 1998, and entitled "Method for Extracting Artifacts in Single Lead Electrocardiography Systems with Pipeline Neural Networks". Both of these provisional applications are hereby incorporated by reference.

FIELD OF THE INVENTION

The present invention relates to automatic external defibrillators (AEDs) and, more particularly, to a manner of extracting artifacts from a patient's ECG signal to more accurately determine the presence of ventricular fibrillation and the necessity of delivering a defibrillation pulse.

BACKGROUND OF THE INVENTION

Automated external defibrillators (AEDs) are used to analyze electrocardiographic (ECG) signals to detect ventricular fibrillation in victims who may be suffering cardiac arrest. The algorithm used within the AED must determine whether to deliver life-saving defibrillation therapy to the victim, and as such, needs to operate with minimal failure. Most AEDs are rate-based in that they compare a patient's monitored cardiac rhythm to preprogrammed nominal values. The problem with rate-based systems, however, is that often artifacts due to motion and/or cardiopulmonary resuscitation (CPR) can occur in the ECG signals potentially causing the AED to operate inappropriately, e.g., delivering a defibrillation pulse where none is needed or not delivering, a defibrillation pulse where one is needed.

As such, there is a need for a ventricular fibrillation detector that incorporates artifact extraction that can be implemented within an AED to reduce the potential for inappropriate operation. The ventricular fibrillation detector preferably operates continuously and is not rate based.

SUMMARY OF THE INVENTION

A ventricular fibrillation detector of the present invention is preferably implemented in an automatic external defibrillator (AED) and substantially addresses the needs described above. The ventricular fibrillation detector generally comprises three detector portions which are operably connected. The first detector portion receives a cardiac rhythm signal in a series of segments and produces an output for each segment that is representative of the presence or absence of ventricular fibrillation. The second detector portion takes the outputs from the first detector portion and produces an output that is representative of a weighted combination of at least two of the output from the first detector portion. The third detector portion receives the output from the second detector portion and compares that output to a predetermined criterion and determines therefrom whether ventricular fibrillation is present.

A method for detecting, ventricular fibrillation generally comprises the steps of: (1) receiving a cardiac signal in a series of segments; (2) determining the absence or presence of ventricular fibrillation in each of said segments; (3) performing a weighted combination of the determinations from at least two of the segments; and (4) comparing the weighted combination against a predetermined criterion and determining therefrom if ventricular fibrillation is present.

DESCRIPTION OF THE PREFERRED EMBODIMENTS

I. Automatic External Defibrillator

Figure 1:
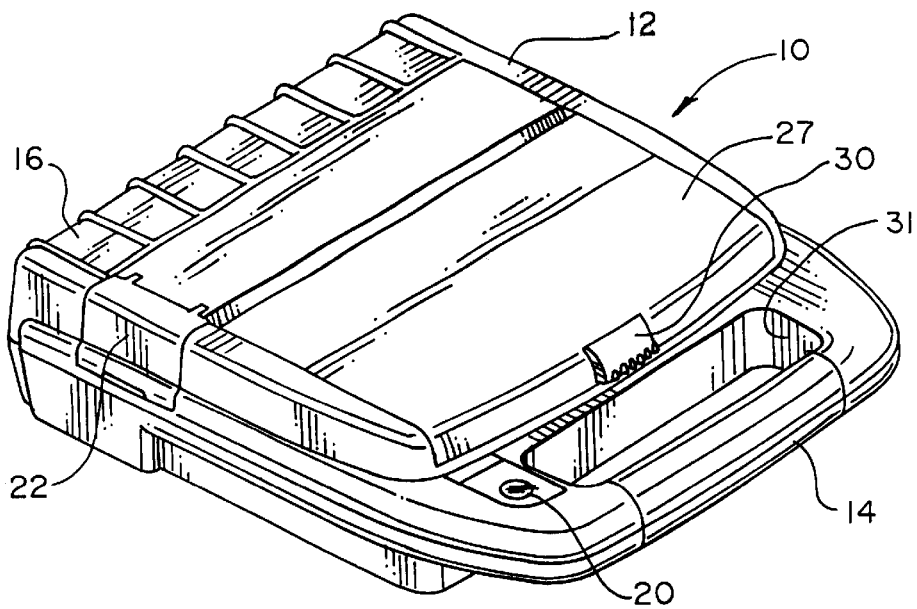
FIG. 1 is a perspective view of an exemplary automated external defibrillator (AED).

An AED 10 is capable of monitoring a patient's cardiac rhythm, detecting cardial defibrillation by using an ventricular fibrillation detector 11 of the present invention, and delivering a series of therapeutic defibrillation shocks if defibrillation is detected. AED 10 is further capable of facilitating alteration of operational parameters as well.

Referring to FIGS. 1–5, an exemplary automated external defibrillator is depicted generally at 10. AED 10 includes case 12. Case 12 further defines carrying handle 14 and battery cover 16. Carrying handle 14 is formed on a front portion of case 12. Case 12 is preferably formed from a synthetic resin in the present embodiment. A battery compartment (not shown) is formed in a rear portion of AED 10. The battery compartment receives and partially encloses a battery pack 16. Battery pack 16 is removably disposed within the battery compartment. Visual maintenance indicator 20 and data access door 22 are located on the outside of case 12 to facilitate access by the operator. Data access door 22 conceals serial connector port 23 and data card slot 24.

Figure 4:
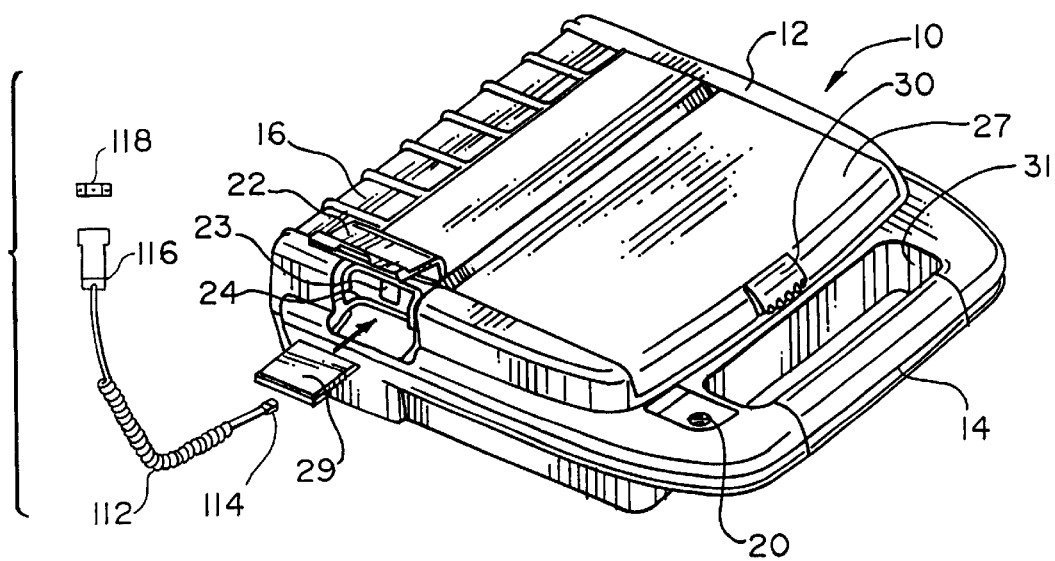
FIG. 4 is a perspective view of the AED of FIG. 1 having the information data card being inserted therein.
Figure 2:
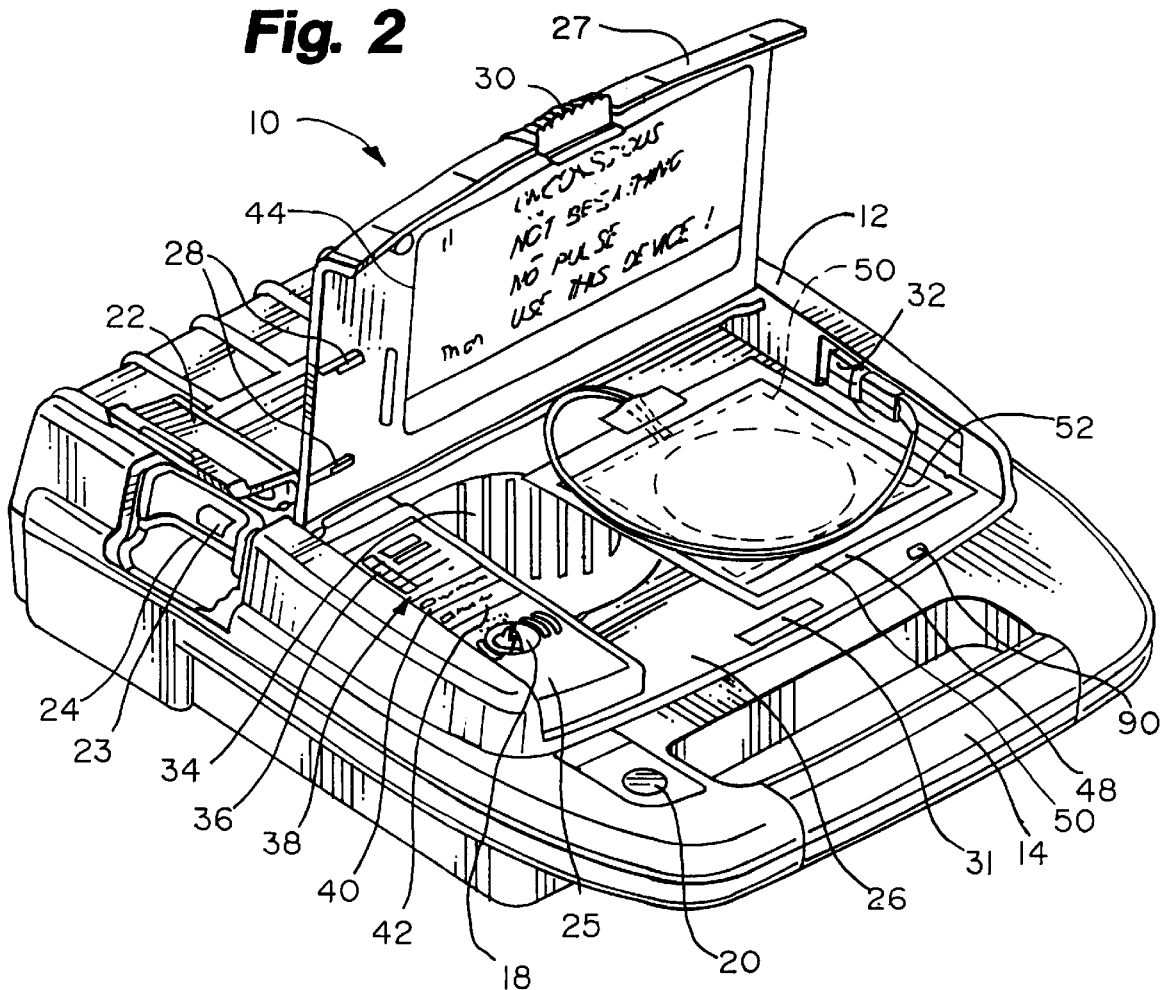
FIG. 2 is a perspective view of the AED of the FIG. 1 having the lid opened.
Figure 3:
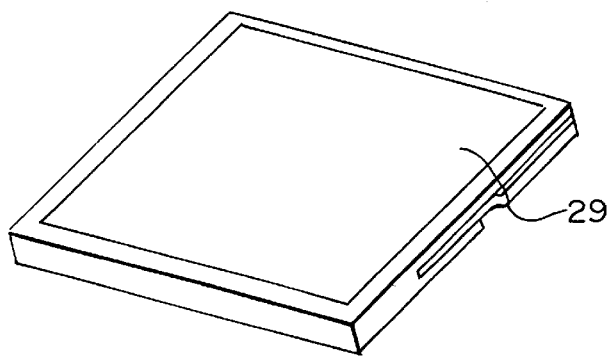
FIG. 3 of is a perspective view of a rescue information data card.

Referring to FIG. 2, case 12 also defines panel 25 and electrode compartment 26 in a top portion thereof. Illuminatable resume/rescue switch 18 is disposed on panel 25, adjacent to electrode compartment 26. Electrode compartment 26 is enclosed by lid 27. Lid 27 is mounted to case 12 by hinges (not shown). Lid 27 covers resume/rescue switch 18 when lid 27 is in a closed disposition, as depicted in FIGS. 1 and 4. Resume/rescue switch 18 is actually a single switch with illuminatable labels. The labels alternatively indicate either a "resume" or "rescue" function. The word "rescue" appears above switch 18 and the word "resume" appears below switch 18. In operation, either "rescue" or "resume" will be illuminated, depending on whether AED 10 is prompting the operator to initiate a rescue or resume operation by activating switch 18. The inside of lid 27 may incorporate data card storage bracket 28. Data card storage bracket 28 is configured for storing a data card such as data card 29.

Data card 29 operationally inserts in data card slot 24. In this embodiment, data card 29 may store rescue information data and recorded sound received from the vicinity of AED 10 during a rescue intervention. In one embodiment, data card 29 is removable from slot 24 and the data stored thereon may be retrieved. The retrieval is then accomplished without removing AED 10 from rescue service. Data card 29 may store new altered defibrillation parameters to be downloaded to AED 10 as well. Data card 29 is commonly known as a flash card and may meet standards approved by the Personal Computer Memory Card International Association (PCMCIA).

Bayonet-type releasable latch 30 holds lid 27 closed when AED 10 is not in use by engaging receiving recess 31. Recess 31 is defined in the floor of electrode compartment 26. Lid 27 is opened by grasping the underside of latch 30, pushing in to disengage latch 30 from recess 31, and lifting upward on latch 30.

Electrode connector 32, speaker 34 and diagnostic display panel 36 are disposed on case 12 proximate electrode compartment 26. Diagnostic display panel 36 is disposed atop panel 25 adjacent illuminatable resume/rescue switch 18. Diagnostic display panel 36 includes visual "Battery Status" indicator light 38, "Electrodes" indicator light 40, and "Service" indicator light 42. Instruction and safety label 44 may be located on an inside surface of lid 27. Electrode pouch 48 may also be disposed within compartment 26. Pouch 48 may hermetically enclose and seal electrodes 50. Electrodes 50 are removably connected to electrode connector 32 by means of leads 52. In this embodiment, electrodes 50 are a pair of electrodes in a sealed package. Electrodes 50 are attached to a patient prior to a rescue intervention procedure.

Figure 5A:
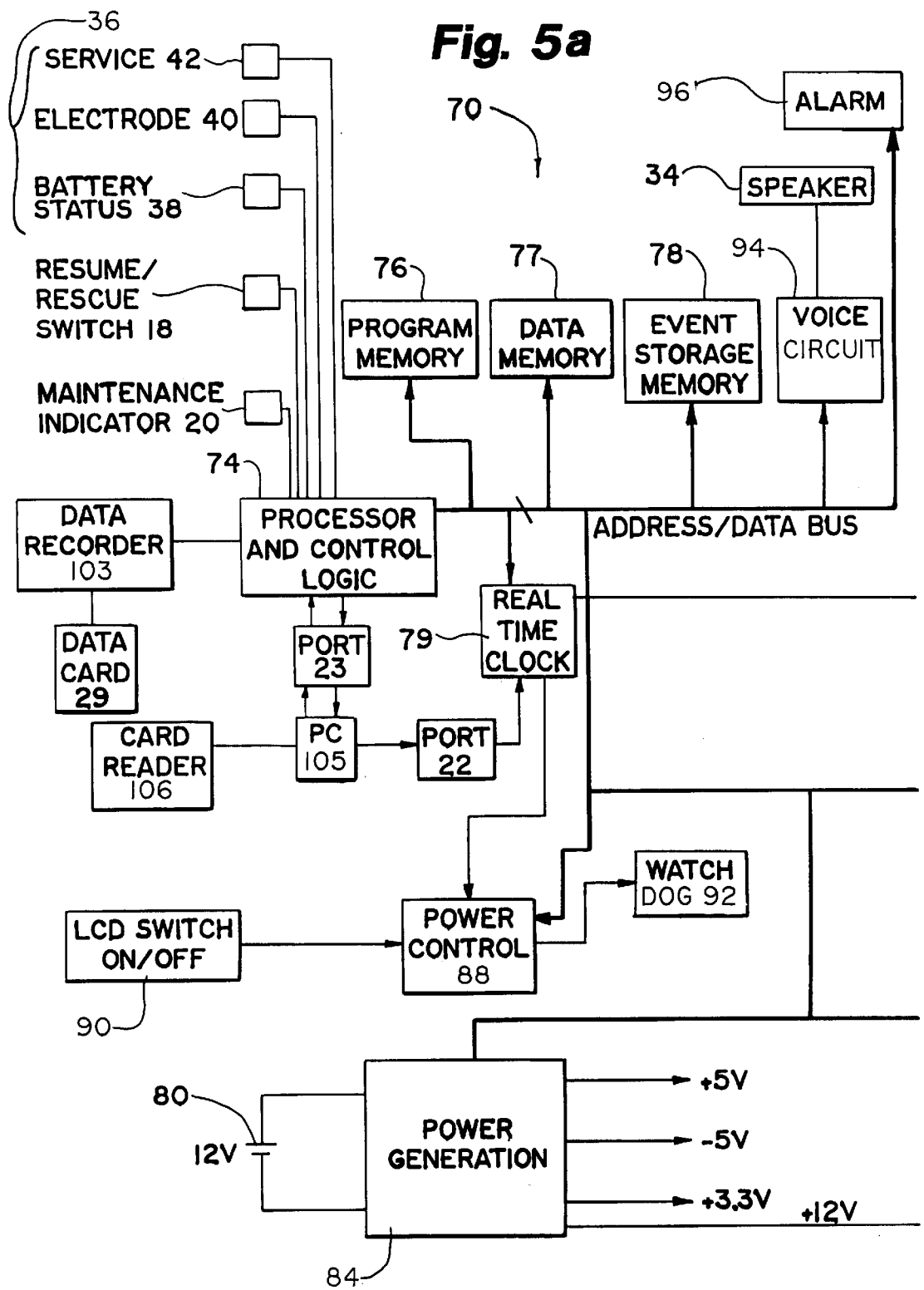
FIG. 5 is a block diagram of an electrical system of the AED of FIG. 1.
Figure 5:
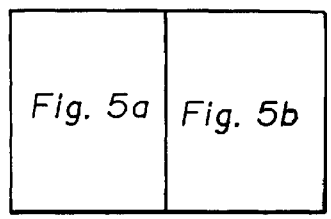
Figure 5B:
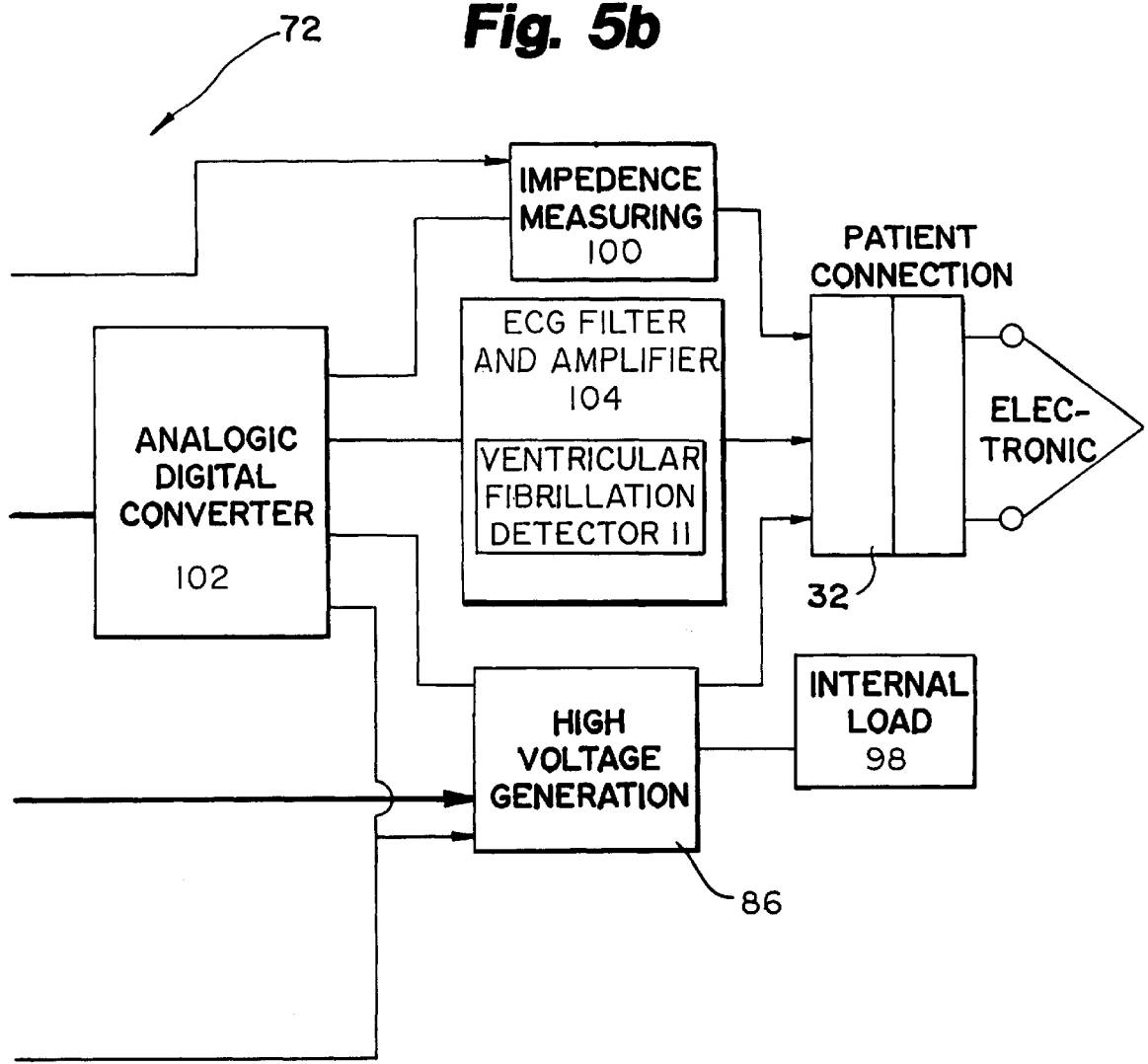

Exemplary electrical system 70 of AED 10 is depicted in the block diagram of FIG. 5. The overall operation of AED 10 is controlled by digital microprocessor-based control system 72. Control system 72, in turn, includes processor 74, program memory 76, data memory 77, event memory 78, and real time clock 79. Processor 74 is interfaced to program memory 76, data memory 77, event memory 78 and real time clock 79. The operating program executed by processor 74 is stored in program memory 76. Data memory 77 is used by processor 74 as a scratch pad memory during the execution of an operating program of AED 10.

Electrical power is provided by battery 80 disposed in battery pack 16. In a particular embodiment, battery 80 is a lithium-sulphur dioxide battery. Battery pack 16 may be removably positioned within the battery compartment of case 12. Battery 80 may include a plurality of interconnected, individual battery cells as desired. Battery 80 is connected to power generation circuit 84. "Battery Status" indicator light 38 indicates the charge status of battery 80 and prompts the operator to replace battery 80 when necessary.

During normal operation, power (generation circuit 84 generates regulated ±5V, and 12V (actually about 5.4V and 11.6V) supplies with electrical power provided by battery 80. A 3.3V supply is generally used to power real time clock 79 and lid switch 90. The 3.3V supply also powers watch dog timer 92 when lid 27 is in a closed position (when AED 10 is in a standby mode). The ±5V output of power generation circuit 84 functions as a back-up battery to power components of electrical system 70 during the execution of self-tests (described below). The ±5V output of circuit 84 also activates maintenance indicators and alarms (also described below). Although not separately shown, power generation circuit 84 includes voltage level sensing, circuits which are coupled to processor 74. These voltage level sensing circuits provide low battery level signals to processor 74.

Power generation circuit 84 is also connected to power control circuit 88 and processor 74. Power control circuit 88 is connected to lid switch 90, watch dog timer 92, real time clock 79 and processor 74. Lid switch 90 is a magnetic reed relay switch in one embodiment or may be a Hall effect sensor. Lid switch 90 provides signals to processor 74 indicating whether lid 27 is open or closed. Serial connector port 23 is coupled to processor 74 for two-way serial data transfer using an RS-232 protocol.

Resume/rescue switch 118 (and the "rescue" and "resume" indications discussed above), "Maintenance" indicator 20, "Battery Status" indicator light 38, "Electrodes" indicator light 40, and "Service" indicator light 42 of diagnostic display panel 36, voice circuit 94 and piezoelectric audible alarm 96 are also connected to processor 74. Voice circuit 94 is connected to speaker 34. In response to voice prompt control signals from processor 74, voice circuit 94 and speaker 34 generate audible voice prompts provided to the operator.

High voltage generation circuit 86 is also connected to and controlled by processor 74. High voltage generation circuits such as circuit 86 are known and disclosed, for example, in the commonly assigned Persson et al., U.S. Pat. No. 5,405,361, which is hereby incorporated by reference. In response to charge control signals provided by processor 74, high voltage generation circuit 86 is operated in a charge mode. During the charge mode of operation, one set of semiconductor switches (not separately shown) causes a plurality of capacitors (not separately shown) to be charged in parallel to a potential of about 400V. Each capacitor is charged by power supplied by power generation circuit 84. Once charged, and in response to discharge control signals from processor 74, high voltage generation circuit 86 is operated in a discharge mode. During discharge, the capacitors are discharged in series by another set of semiconductor switches (not separately shown) to produce high voltage defibrillation pulses. The defibrillation pulses are applied to the patient by electrodes 50, via electrode connector 32. Electrode connector 32 is connected to high voltage,e generation circuit 86. Under certain circumstances (described below), processor 74 causes high voltage generation circuit 86 to be discharged through internal resistive load 98 rather than connector 32.

Impedance measuring circuit 100 is connected to electrode connector 32 and real time clock 79. Impedance measuring circuit 100 is also interfaced to processor 74 through analog-to-digital (A/D) converter 102. Impedance measuring circuit 100 receives a clock signal with a predetermined magnitude from clock 79 and applies the signal to electrodes 50 through connector 32. The magnitude of the clock signal received back from electrodes 50 through connector 32 is monitored by impedance measuring circuit 100. An impedance signal representative of the impedance present across electrode connector 32 is then generated by circuit 100 as a function of the ratio of the magnitudes of the applied and received clock signals (i.e., a measure of the attenuation of the applied signal). For example, if the conductive adhesive on electrodes 50 is too dry, if electrodes 50 are not properly connected to connector 32, or if electrodes 50 are not properly positioned on the patient, a relatively high resistance (e.g., greater than about 200 ohms) will be present across connector 32. The resistance across connector 32 will be between about 25 and 175 ohms when fresh electrodes 50 are properly positioned on the patient with good electrical contacts. The signal representative of the impedance measured by circuit 100 is digitized by A/D converter 102, then relayed to processor 74.

AED 10 also includes data recorder 103 and electrocardiogram (ECG) filter, which comprises ventricular fibrillation detector 11, and amplifier 104. Data recorder 103 is interfaced to processor 74. Data recorder 103 is positioned internally within AED 10 adjacent to data card slot 24, so as to be ready to accept data (rescue information) card 29. ECG filter and amplifier 104 is connected between electrode connector 32 and A/D converter 102. The ECG or cardiac rhythm of the patient is sensed by electrodes 50 on the patient and processed by ECG filter, as described below in section 11, entitled "Ventricular Fibrillation Detector" and by amplifier 104 in a conventional manner, then digitized by A/D converter 102 before being relayed to processor 74.

The rescue mode of operation of AED 10 is initiated when an operator opens lid 27 to access electrodes 50. An opened lid 27 is detected by lid switch 90. I-id switch 90 functions as an on/off switch for AED 10. In response to lid switch 90 being activated when lid 21 is opened, power control circuit 88 activates power (generation circuit 84 and initiates the rescue mode operation of processor 74. Processor 74 then begins its rescue mode operation by: 1) switching maintenance indicator 20 to a maintenance required state (a red visual display in one embodiment); 2) flashing the "rescue" light associated with resume/rescue switch 18 and the indicator lights on diagnostic display panel 36; and 3) performing a lid opened self-test.

During the lid opened self-test, checks performed by processor 74 include: 1) the charge state of battery 80; 2) the interconnection and operability of electrodes 50 (if the electrode test enabled); 3) the state of event memory 78; 4) the functionality of real time clock 79; and 5) the functionality of A/D converter 102. The charge state of battery 80 is checked by monitoring, the voltage level signals provided by power generation circuit 84 and comparing these voltage level signals to predetermined nominal values. If battery 80 is determined to have a low charge, the "battery status" indicator 38 on diagnostic display panel 36 will indicate the sensed status. If the electrode self-test is conducted, the interconnection and operability of electrodes 50 are checked by monitoring the impedance signals provided by impedance measuring circuit 100. If electrodes 50 are missing or unplugged from connector 32, if electrodes 5(0 are damaged, or if the conductive adhesive on electrodes 50 is too dry, processor 74 will illuminate "Electrodes" indicator light 40 on diagnostic display panel 36.

Also, during the lid opened self-test, processor 74 accesses event memory 78 to determine whether data from a previous rescue operation are still stored therein. If data from a previous rescue are still present, processor 74 causes the "resume" indicator associated with resume/rescue switch 18 on diagnostic panel 36 to be illuminated and initiates the generation of a "Clear Memory" voice prompt. If resume/rescue switch 18 is pressed by the operator following the activation of these indicators, processor 74 clears event memory 78 and proceeds with its rescue mode of operation. The functionality of real time clock 79 and A/D converter 102 are checked by monitoring the outputs of these circuit elements for expected signals. Diagnostic display panel "Service" light 42 is illuminated by processor 74 if faults are identified in real time clock 79 or in A/P converter 102.

If the lid opened self-test is successfully completed, processor 74 switches maintenance indicator 20 to an operational state and initiates the rescue mode of operation of AED 10. In the rescue mode of operation voice circuit 94 generates audible voice prompts through speaker 34 to guide the operator through the operations of AED 10 and, if necessary, delivery of a defibrillation pulse to the patient. AED 10 determines its rescue mode steps of operation by monitoring the impedance across electrode connector 32 and the patient's cardiac rhythm.

Closing lid 27 after rescue mode operation activates processor 74 to initiate and perform a lid closed self-test. During the lid closed self-test, processor 74 performs a comprehensive check of the status and functionality of AED 10 including: 1) the state of event memory 78; 2) the functionality of real time clock 79; 3) the functionality of A/D converter 102; 4) the functionality of program memory 76, data memory 77, and event memory 78; 5) the charge state of battery 80; and 6) the interconnection and operability of electrodes 50 (if enabled to do so). The state of event memory 78, the state of battery 80, the interconnection and operability of electrodes 50, and the functionality of real time clock 79 and A/D converter 102 are checked in a manner identical to that described above with reference to the lid opened self-test.

Conventional memory test routines are also implemented to check the functionality of program memory 76, data memory 77 and event memory 78. Maintenance indicator 20 is switched to its maintenance required state by processor 74 if faults are identified during the lid closed self-test. No audible alarms are actuated if faults are identified in the charge state of battery 80 or the interconnection or functionality of electrodes 50 during(g the lid closed self-test.

A daily self-test is also initiated and performed by processor 74 at a predetermined time each day (i.e., every twenty-four hours). During the daily self-test, processor 74 performs all the component check operations described above that are performed during the lid opened and lid closed self-tests. In addition to illuminating the appropriate lights on diagnostic display panel 36, processor 74 leaves maintenance indicator 2(0 in a maintenance required state if faults are identified during the daily self-test.

Processor 74 also initiates and performs a weekly self-test at a predetermined time one day each week. During the weekly self-test, processor 74 performs all the component check operations described above that are performed during the daily self-test. In addition, processor 74 causes high voltage generation circuit 86 to sequentially operate in its charge and discharge modes, the charge being, directed to internal resistive load 98. When high voltage generation circuit 86 is operating in a charge mode, processor 74 monitors the time required to charge the circuit's capacitors and the capacitor voltage. A fault is identified if either time is outside nominal conditions. Maintenance indicator 20 and alarm 96 are actuated in the manner described above if any faults are identified during the weekly self-test. All performed test and patient data may be recorded in event memory 78.

Watch dog timer 92 is set to time watch dog time-out periods of about thirty hours (i.e., a period greater than the twenty-four hour periods between daily self-tests). Watch dog timer 92 is reset by processor 74 at the beginning of each daily self-test and each time lid 27 is opened. In the event control system 70 malfunctions and watch dog timer 92 times out, internal hardware switches maintenance indicator 20 to the maintenance required state and actuates alarm 96 to alert the operator to the fact that AED 10 requires maintenance.

AED 10 facilitates archival storage of rescue information. Data representative of the operation of AED 10 and patient data may be stored in event memory 78 during rescue mode operation. However, if data card 29 is inserted into card slot 24 before the beginning of a rescue attempt, the rescue information is automatically recorded by data recorder 103 onto data card 29, thereby also facilitating archival storage of rescue information. Stored data representative of the operation of AED 10 may include the real time of the occurrence of each of the following events: 1) the placement of electrodes 50 on the patient, 2) the initiation of the cardiac rhythm analysis voice prompt, 3) the initiation of the charging voice prompt, 4) the completion of the charge mode operation of high voltage generation circuit 86, and 5) the actuation of the resume/rescue switch 18 in the rescue mode. The actual time base of the patient's cardiac rhythm (ECG information) may also be stored. Data representative of the patient may include the monitored cardiac rhythm, key events detected during the rescue operation, and sound occurring within the vicinity of AED 10.

Following a rescue, the stored data may be retrieved from event memory 78 through the use of computer (PC) 105 interfaced to serial connector port 23. The details of this interface are discussed below. Real time clock 79 can also be set through the use of PC 105 interfaced to port 23. If the rescue data were stored on data card 29 and data card 29 remains in slot 24, the data may also be retrieved through the use of PC 105 interfaced to serial connector port 23. Alternatively, data card 29 may be removed from slot 24 and inserted into an appropriate card reader 106, directly connected to PC 105, such as a PCMCIA type I card reader.

Upon the completion of each lid opened, lid closed, daily and weekly self-test, processor 74 causes a record of the self-test to be stored in event memory 78. Each stored record includes data representative of the date and time of the test and the results of the test. The test results are recorded in the form of a code or other description indicating whether all the functions, components and component status states passed the test, or indicating the nature of any identified faults. In one embodiment, only the records of the twenty most recently performed tests are stored in memory 78. The stored self-test records may be retrieved from memory 78 through PC 105 interfaced to serial connector port 23. Each self-test is powered by the battery pack. The battery pack may also be coupled to real time clock 79 to continuously provide power thereto.

II. Ventricular Fibrillation Detector

Figure 6:
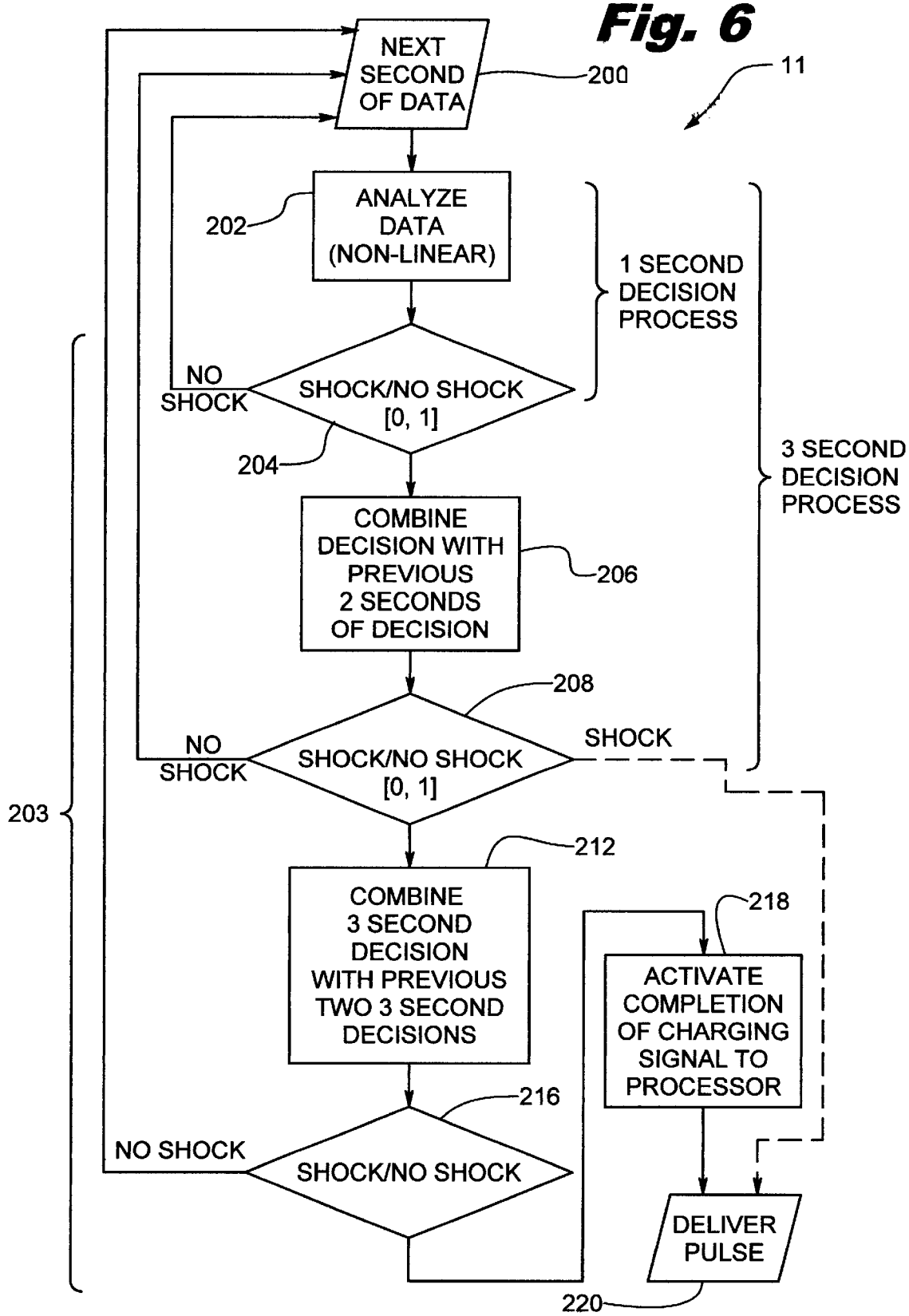
FIG. 6 is a flow diagram of the artifact extraction algorithm of the present invention.

Referring to FIG. 6, a flow diagram of the ventricular fibrillation detector 11 of the present invention is depicted. As shown, ventricular fibrillation detector 11 comprises a filter that is preferably a non-linear, non-stationary time series filter that performs adaptively, e.g., with a complex-domain neural network, on a continuous basis. For example, ventricular fibrillation detector 11 preferably includes an ongoing, continuous operation based on a sliding window of three seconds in three one-second intervals (tapped time-delay filter), to detect and extract artifacts from a patient's ECG signal. As such, the filter preferably comprises a cascade combination of a first non-linear section 202 and a second linear section 203 as indicated.

With electrodes 50 secured to a patient and the patient's cardiac rhythm detected by AED 10, the ventricular fibrillation detector operates as follows. First, per input block 200, one second of the patient's cardiac rhythm is read. Next, per operation block 202, the patient's cardiac rhythm data is analyzed preferably using a complex-domain neural network (230), which is described in detail below, to determine if that second of rhythm data represents a rhythm requiring the delivery of a defibrillation pulse. Next, per decision block 204, a decision based on the analysis of the one second of data is made to deliver a defibrillation pulse ("shock") or not deliver a defibrillation pulse ("no shock"). If the decision is "no shock", the method flow is returned back to input block 200 where another second of the patient's cardiac rhythm data is continuing to be read.

If the decision is "shock", the method flows forward to operation block 206 wherein the decision of decision block 204 from the last second of patient data is combined, with the previous two seconds of decisions; the combination being a weighted average of the three decisions. Three seconds of "shock/no shock" decisions based on the patient's cardiac rhythms have now been combined and are input to decision block 208. Decision block 208 compares the weighted average to a predetermined value to determines if the three seconds of decisions indicate a decision to "shock", e.g. weighted average greater than predetermined value, then shock. If the three seconds of decisions do not so indicate, the method flow is returned back to input block 200 where another second of the patient's cardiac rhythm data is continuing to be read.

If the three seconds of decisions do indicate a "shock" decision a signal may sent to processor 74 to activate charging circuit 86, see operation block 218, and a defibrillation pulse is delivered to the patient, see operation block 220. Alternatively, the decision making process may flow forward yet again to operation block 212 wherein the decision of decision block 208 from the last three seconds of patient data is combined with the previous two decisions from block 208 by weighted average, which is representative of the six seconds of patient data previous to the last three seconds of patient data. As such, nine seconds of patient data, that is nine one-second decisions and three three-second decisions are combined. The combined three-second decisions from block 212 are then input to decision block 216 and compared with a predetermined value, e.g. weighted average greater than predetermined value then deliver defibrillation pulse. If three three-second decisions do not indicate a "shock" decision the method flow is returned back to input block 200 where another second of the patient's cardiac rhythm data is continuing to be read.

If the three three-second decisions from block 212 do indicate a "shock" decision, a signal is sent to processor 74 to activate charging circuit 86, see operation block 218, and a defibrillation pulse is delivered to the patient, see operation block 220.

Ventricular fibrillation detector 11, as described above, is based on one-second, three-second, and nine-second time windows, however, it should be noted that other lengths of time windows may be used without departing from the spirit or scope of the invention.

Further, ventricular fibrillation detector 11, as described uses a weighted average filter, however, it should be noted that numerous other types of filters may be used without departing from the spirit or scope of the invention. For example, a moving average filter, an autoregressive filter, an autoregressive moving average filter, a digitally implemented analog prototyped IIR filter, a Butterworth filter, a type I Chebyshev filter, a type II Chebyshev filter, an elliptic filter, a Bessel filter, a Kalman filter, a multivariate linear predictor, a multivariate nonlinear predictor, or a bayesian predictor may be used.

The accuracy of ventricular fibrillation detector 11 of the present invention, utilizing the complex-domain neural network (230), was validated by comparing its extraction capabilities against the extraction capability of a forward linear predictor based on standard Wiener filter theory and its mean-square error criterion. Both methods were trained and tested within the framework of a standard AED detection and decision algorithm. Greater than 1000 rhythm strips from the MIT-BIH (Massachusetts Institute of Technology—Beth Israel Hospital) database, and the SurVivaLink arrythmia and resuscitation library, were used to train and test the methods. Artifacts were simulated using AED-recorded artifact data comprising patient motion, muscle noise, and agonal breathing.

The cascade combination of complex-domain neural network (230) and tapped delay-line filter accurately identified and extracted ECG signal artifact. The ventricular fibrillation detector significantly reduced the false detection rate compared to the standard AED detection method. Further, the ventricular fibrillation detector of the present invention provided better extraction capabilities than the standard forward linear predictor using mean-squares.

III. Analysis of Cardiac Rhythm Data—Neural Network

Figure 7:
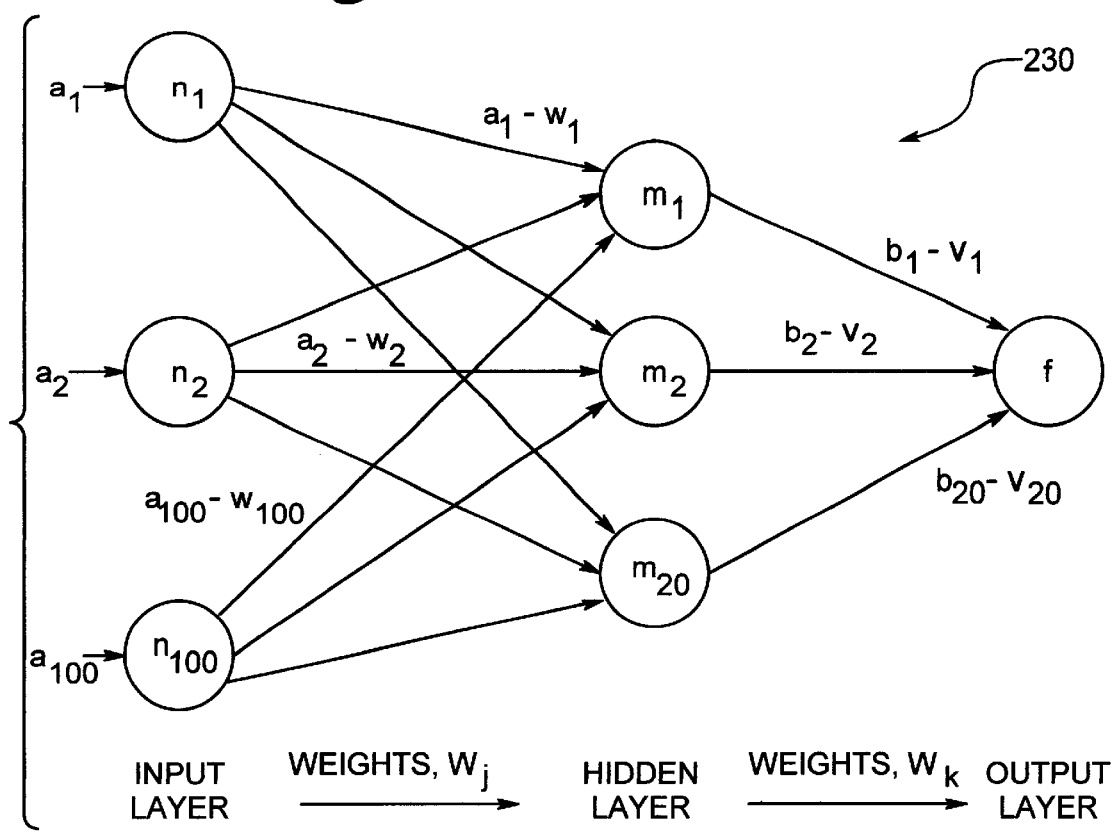
FIG. 7 is a schematic diagram of a non-linear section of a filter of the present invention.

The analysis, per operation block 202 of ventricular fibrillation detector 11, of patient cardiac rhythm data is preferably performed with a pipelined complex-domain neural network 230 as depicted in FIG. 7. Neural network 230 is designed for high computational efficiency and linearizes the ECG input data for the linear section 203 of the filter. Complex-domain neural network 230 learns on-line to adapt to the specific statistical variations of the incoming ECG signal while performing its filtering role. As shown in FIG. 7, neural network 230 is preferably a feed forward neural network, however it should be noted that other types of neural networks may be used without departing from the spirit or scope of the invention. In this feed forward neural network, information passes only in one direction through the network, i.e., from the input layer to the hidden layer and from the hidden layer to the output layer, as indicated by the arrows in FIG. 7. Note that there are no communications among nodes in a layer.

The basis of a neural network is that it is a learning or trainable network, a complex-domain neural network implicitly learns frequency content (phase). As such, prior to the first actual use of AED 10 in an emergency situation, complex-domain neural network 230 has preferably been designed and trained with training/test data. For example, rhythm strips from the MIT-BIH database, the SurVivaLink arrythmia and resuscitation library, and specifically generated artifacts, which are simulated using AED-recorded artifact data comprising patient motion, CPR, muscle noise, and agonal breathing, may be, and are preferably used to train neural network 230.

In designing neural network 230, the number of nodes in each layer must be determined. It has been found that the preferable number of nodes in each layer to achieve fast and effective operation are as follows: (1) input layer –1000 nodes (designated n=1–100); (2) hidden layer—20 nodes (designated m=1–20); and (3) output layer—a single node. It should be noted, however, that more or less nodes could be used per layer without departing from the spirit or the scope of the invention.

Further, in designing, neural network 230, it must be determined which activation function the hidden and output nodes will use (input nodes allow the input to pass straight through and therefore use no activation function). Numerous types of activation functions may be used without departing from the spirit or scope of the invention. However, the preferred activation function is a squashing function which may be defined, in general nomenclature as follows:

$$\text{Squashing Function} = f(x+yi) = \tan h(x) + \tan h(y)i \quad (1)$$

The above squashing function is a good activation function in the complex-domain because both its real and imaginary parts are continuously differentiable with respect to the real and imaginary parts of the domain variable. Further, its magnitude is bounded and approaches those bounds rapidly as the magnitude of the domain variable increases. Additionally, the function is approximately linear when the magnitude of the domain variable is small.

To train neural network 230, the outputs, or in other words, the activation level for each of the hidden and output nodes must be defined. Defining the activation level is a two-step process. The first step of the process comprises defining the net input to each hidden and output node. The net input represents the sum of the weighted inputs to each node plus a threshold, or bias, value. As such, the net input to a hidden layer node may be defined as follows:

$$\text{Net Input}_H = \sum_{j=1}^{n} a_j w_j + \Theta_j \quad (2)$$

where:

n=the number of nodes in the input layer, e.g. 100;

$a_j$=the output value of the jth input node;

$w_j$=the jth weight to be applied to the output value of the jth input node; and $\Theta_j$=the jth threshold value for the jth input node.

While the net input to the output layer node may be defined as follows:

$$\text{Net Input}_O = \sum_{k=1}^{m} b_k v_k + \Gamma_k \quad (3)$$

where:

m=the number of nodes in the hidden layer, e.g. 20;

$b_k$=the output value of the kth hidden node;

$v_k$=the kth weight to be applied to the output value of the kth hidden node; and $\Gamma_k$=the kth threshold value for the kth hidden node.

The second step in defining the output, or activation level, for each of the hidden and output nodes is to apply the activation function (the squashing function of equation 1) to each of the net inputs. As such, the output of each of the hidden nodes may be defined as follows:

$$\text{Output}_H = f(\text{Net Input}_H) = bk \quad (4)$$
$$= f\left(\sum_{j=1}^{n} a_j w_j + \Theta_j\right).$$

While the output of the single output node may be defined as follows:

$$\text{Output}_O = f(\text{Net Input}_O) \quad (5)$$

$$= f\left(\sum_{k=1}^{m} b_k v_k + \Gamma_k\right).$$

Figure 8:
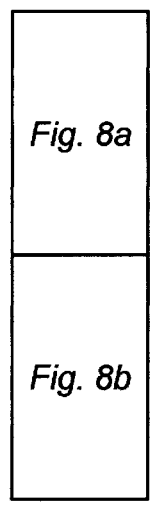
FIG. 8 is a flow diagram depicting the training of a neural network of the present invention.
Figure 8A:
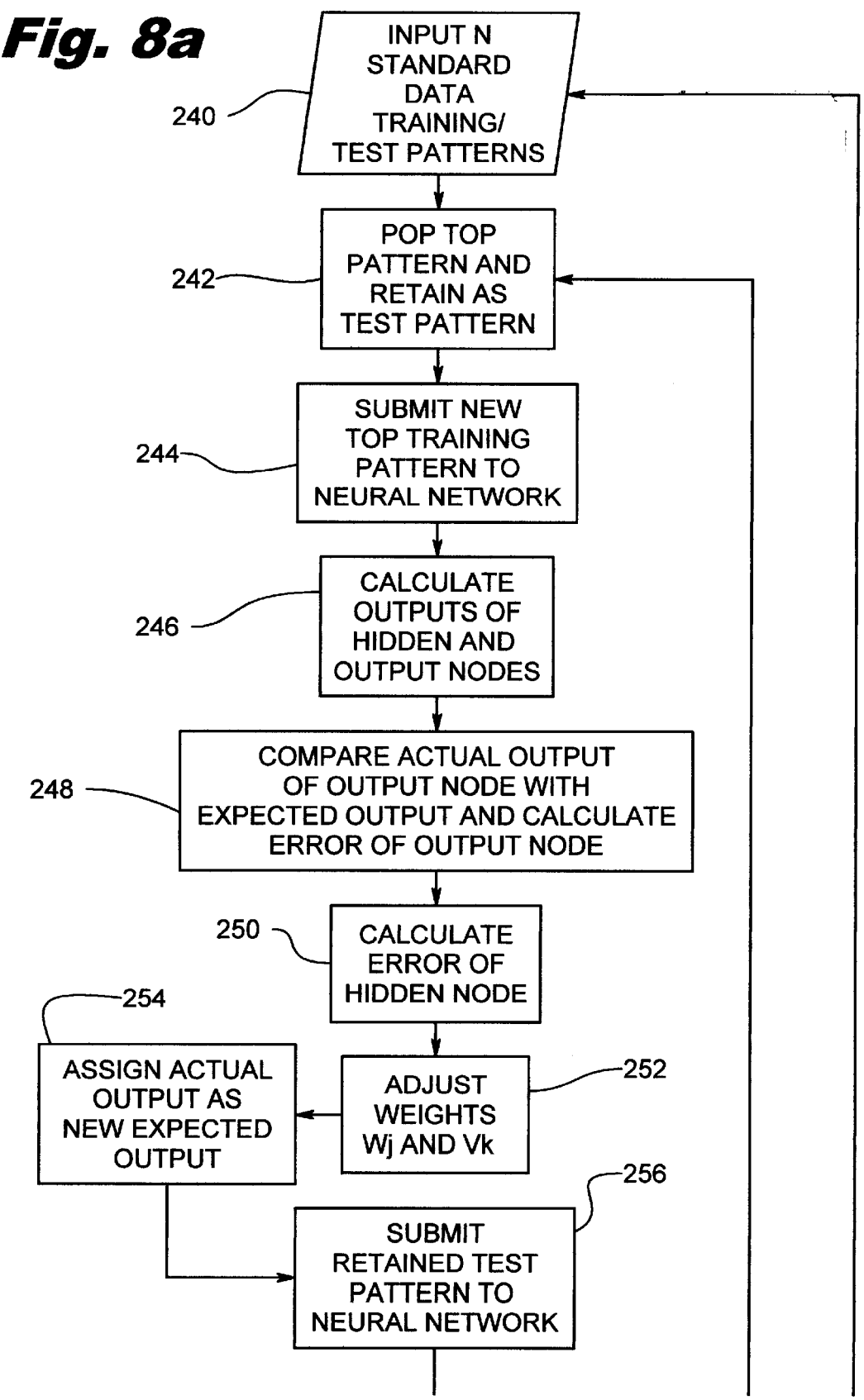
Figure 8B:
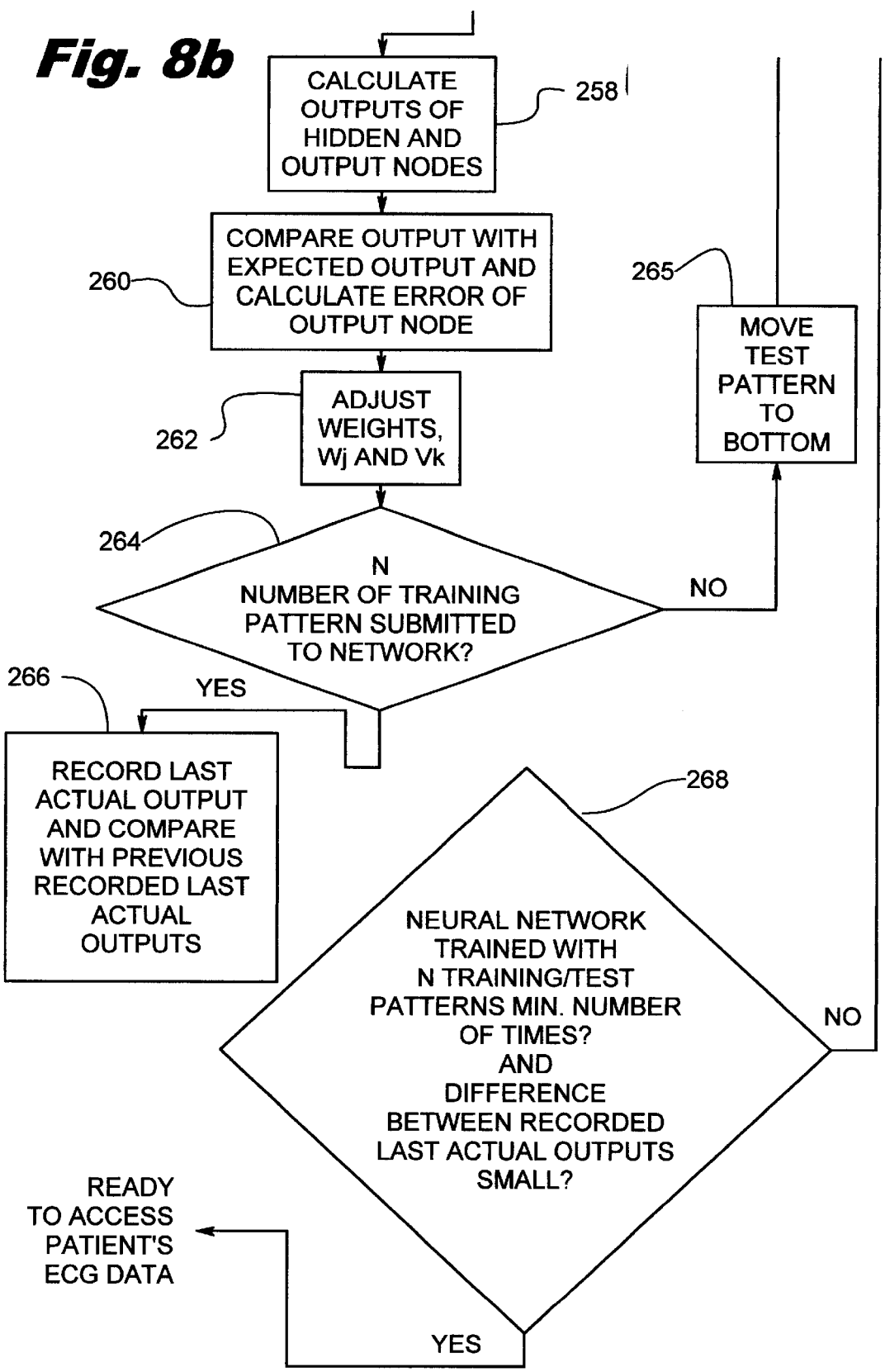

With the activation levels defined, the training of neural network 230 may begin. A flow chart showing the preferred training sequence of neural network 230 is depicted in FIG. 8. However, prior to running the first set of training patterns, each of the thresholds ($\Theta_j$ and $\Gamma_k$) are preferably set to a very low value, e.g. 0.05. Additionally, each of the weights ($w_j$ and $v_k$) are preferably randomly assigned a value between −1 and 1, the expected neural network output is assigned a value of 0, and the number (N) of training/test patterns that will be used is determined.

Next, the training/test patterns are input to the complex-domain neural network. As indicated earlier the training/test data preferably includes data taken from rhythm strips from the MIT-BIN database and artifacts, which are simulated using AED-recorded artifact data comprising patient motion, CPR, muscle noise, and agonal breathing. While the number of test patterns used to train neural network 230 may vary, it is preferred that at least 1000 test patterns of rhythms and artifacts be used.

Note that prior to the input of the training/test patterns to complex-domain neural network 230 the data within the patterns has been appropriately formatted. First, the at least 1000 database patterns have been processed to extract and create at least 1000 rhythm data files, which will teach the neural network to recognize a normal sinus rhythm and asystole, at least 1000 ventricular fibrillation data files, which will teach the neural network to recognize ventricular fibrillation rhythms, various ventricular tachycardia rhythms, i.e., poly-, supra-, monomorphic, and at least 1000 noise data files, which will teach the neural network to recognize artifact, e.g. cardiopulmonary resuscitation artifact, motion artifact, etc. Next, a large segment of data from each of the data files is extracted and divided into 100 points per one second of data (the number of data points matching the number of input layer nodes) to produce the training/test patterns containing real data.

The next step prior to input of the training/test patterns to complex-domain neural network 230 is the standardizing of the real data with mean and variance scaling. That is, the mean of the 100 points of data is calculated as is the standard deviation of the data. Then, each point of the 100 points of real data is standardized to a mean of 0 and a deviation of 1. As such, each point of standardized data may be defined as follows:

$$\text{Std. Data} = \frac{\text{Real Data} - \text{Mean}}{\text{Standard Deviation}}. \quad (6)$$

With the data within each point of each training/test pattern standardized, reference may now be made to the flow chart of FIG. 8 to understand the actual training of complex-domain neural network 230. Per input block 240, N standardized-data training/test patterns are input. Thinking of the N training/test patterns as being in a stack formation, the top training pattern is popped from the stack and retained as a test pattern, see operation block 242. With the top training pattern removed and retained, the new top training pattern is preferably submitted to neural network 230, see operation block 244. Next, per operation block 246, the outputs of the nodes of the hidden and output layers of neural network 230 are calculated according to equations 4 and 5, provided above.

The actual output of the output node is then compared with the expected output and the error of the output node is calculated per equation 7 below, see operation block 248.

$$\text{Error}_O = \frac{1}{n} \sum_p ((a_{pr} - t_{pr})^2 + (a_{pi} - t_{pi})^2)^{0.5} \quad (7)$$

where:

n=the number of nodes in the input layer;

a=actual Output;

t=expected or target output; and r—real, i-imaginary.

The partial derivative of the output error with respect to the real portion of the actual output and the partial derivative of the output error with respect to the imaginary portion of the actual output are defined by equations 8 and 9, respectively, below:

$$\frac{\partial E_O}{\partial a_r} = \frac{a_r - t_r}{n((a_r - t_r)^2 + (a_i - t_i)^2)^{0.5}} \quad (8)$$

$$\frac{\partial E_O}{\partial a_i} = \frac{a_i - t_i}{n((a_r - t_r)^2 + (a_i - t_i)^2)^{0.5}} \quad (9)$$

The error of the nodes of the hidden layer are then preferably calculated, see operation block 250, per a recursive method using the output error and partial derivatives defined above. This recursive method is called complex-domain back propagation. It operates to minimize the mean absolute error of the outputs and is well understood in the art. Specifically, this method is described in the following publications, which are hereby incorporated by reference: (1) *Signal and Image Processing, with Neural Networks A C++ Sourcebook,* by Timothy Masters (see pages 11–80); (2) *Learning Internal Representations by Error Propagation,* by D. E. Rumelhart, et al. (see pages 318–353); and (3) *Artificial Neural Systems— Foundations, Paradigms, Applications and Implementations,* by P. Simpson (see pages 100–126).

With the errors of the nodes of the hidden and output layers calculated, the weights applied to the inputs of the nodes of the hidden and output layers, $w_j$ and $v_k$, respectively, are adjusted, per operation block 252. The manner of adjusting the weights is also well understood in the art and is also described in the publications listed in the paragraph above.

With the weights adjusted, the calculated output of the output node is assigned as the new expected output, per operation block 254. Next, per operation block 256, the retained test pattern is submitted to neural network 230 and the outputs of the nodes of the hidden and output layers are calculated according to equations 4 and 5 above, see operation block 258. The new calculated output of the output node is then compared with the expected output, and the error of the output node is calculated according to equation 7 above, see operation block 260. Once again, the weights of the output node and the hidden nodes are adjusted via two-sided back propagation methods see operation block 262.

Decision block 264 then asks whether all of the N training/test patterns have been submitted to neural network 230. If not, the retained test pattern is moved to the bottom of the stack of training/test patterns, per operation block 265, and the flow of the training procedure of neural network 230 returns to operation block 242. If all of the N training/test patterns have been submitted to neural network 230, the last calculated output of the output node is recorded, per operation block 266.

Decision block 268 then asks two questions: (1) Whether neural network 230 has been trained with the N training/test patterns a predetermined minimum number of times, e.g., 5 times; and (2) Whether the difference between the recorded last calculated outputs, e.g., 5 recorded last calculated outputs, is less or equal to a predetermined error in the trained neural network 230. If the answer to either question is no, the flow of the training procedure of neural network 230 is returned to operation block 240 for another round of training with N training/test patterns. However, if the answer to both questions is yes, neural network 230 has been sufficiently trained, is ready to accept actual patient ECG data provided by electrodes 50 of AED 10, and adaptively operate to differentiate between various ECG rhythms.

It should be noted that there is a one-to-one correspondence between neural networks and fuzzy sets. Therefore, the complex-domain 230 neural network maybe replaced with an equivalent one-second detector that contains and operates the fuzzy set rules that implement an equivalent detector.

IV. Analysis of Cardiac Rhythm Data—Alternative to Neural Network

Figure 9:
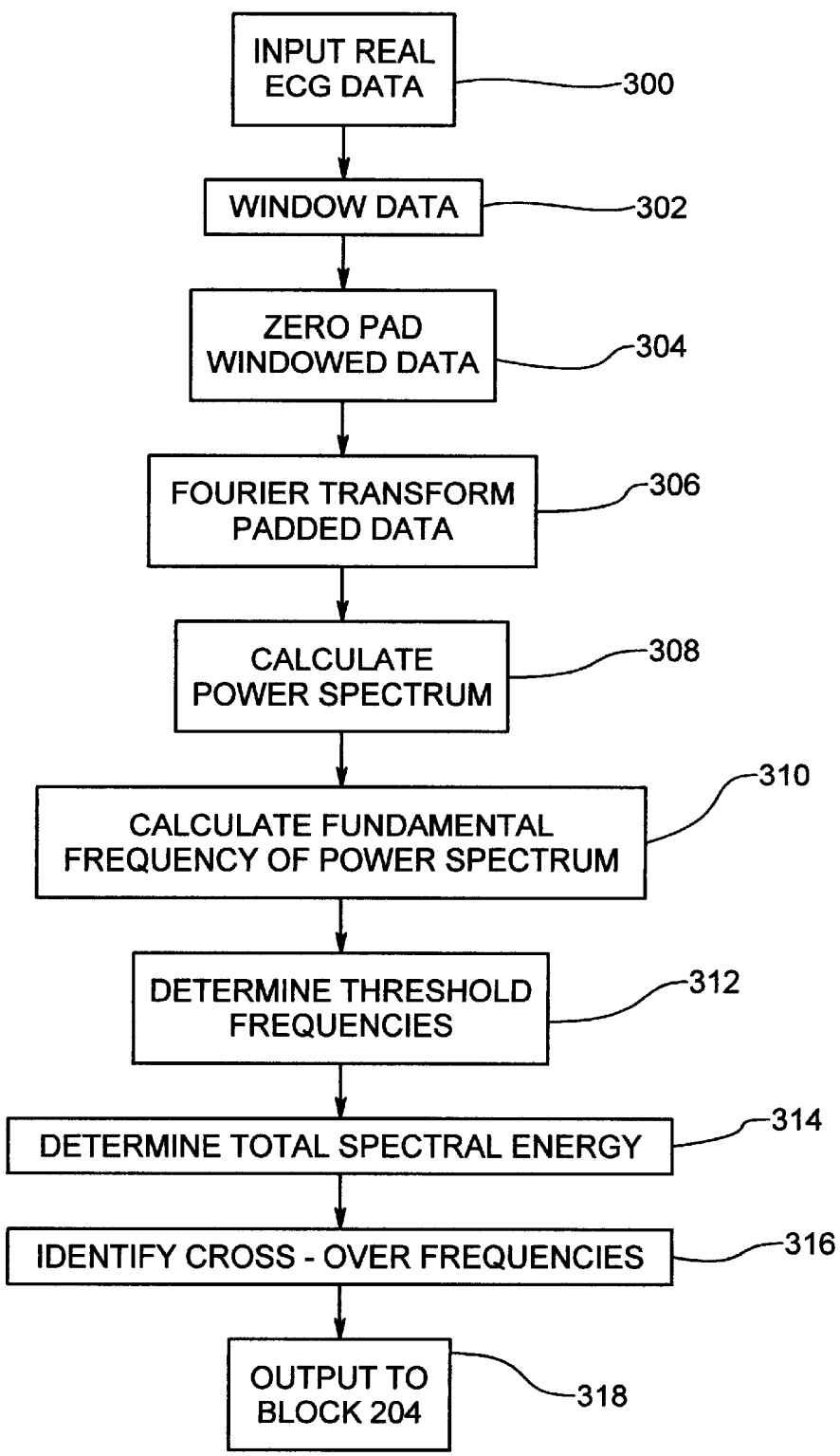
FIG. 9 is a flow diagram of the operation of a spectrum analyzer of the present invention.

While the ventricular fibrillation detector II of the present invention preferably uses an adaptive neural network to analyze patient ECG data, alternative methods of analyzing ECG data may also be used. For example, a spectrum analyzer may be used to analyze a patient's ECG data. FIG. 9 provides a flow chart depicting the operation of a spectrum analyzer on ECG data.

Per input block 300, ECG data, in real data format is input to the analyzer. Next, per operation block 302, the real data is windowed using a Kaiser-Bessel window. The alpha (the adjustment for side lobe level versus main lobe width compromise) is preferably in the range of 2–4, and more preferably 4. Of course other windowing functions may be used without departing from the spirit or the scope of the invention. The windowed data is then zero padded in order to smooth the Fourier transform, per operation block 304.

Next, per operation block 306, the windowed and padded data is transformed from the time domain to the frequency domain via a Fourier transform. The power spectrum of the frequency domain data is then computed, see operation block 308.

The fundamental frequency of the power spectrum is also computed, see operation block 310, based on a preferred sampling rate of the data of 100 data points per second. Of course, other sampling rates may be used without departing from the spirit or scope of the invention. Next, the threshold frequencies, the frequencies at which the power spectrum energy is greater than a predetermined energy threshold are determined across successive time intervals, e.g. 1 second time intervals, however, other time intervals may be used without departing from the spirit or scope of the invention.

Per operation block 314, the power spectrum of the ECG data is then integrated to determine the total spectral energy and, per operation block 316, the cross-over frequencies, i.e., the frequencies with accumulated spectral energy is greater than a predetermined percent, e.g., 99%, of total spectral energy are calculated. The cross-over frequencies determine if the delivery of a defibrillation pulse is or is not required, this determination is then input to decision block 204 (FIG. 6).

Other alternatives to the complex-domain feed forward neural network may be used without departing from the spirit or scope of the invention. For example, a complex-domain recurrent neural network, a power spectral density analyzer, a cross-spectral density analyzer, a coherence analyzer, a cepstrum analyzer, and a time-frequency domain analyzer.

The present invention may be embodied in other specific forms without departing from the essential attributes thereof; therefore, the illustrated embodiments should be considered in all respects as illustrative and not restrictive, reference being made to the appended claims rather than to the foregoing description to indicate the scope of the invention.

What is claimed is:

1. An automatic external defibrillator (AED) having a ventricular fibrillation detector, comprising:
   first detector means for receiving a cardiac rhythm signal, wherein said cardiac rhythm signal is submitted to said first detector means in a series of segments, and for producing a first output for each segment, wherein said first output is representative of the absence or presence of ventricular fibrillation;
   second detector means operably connected to said first detector means, said second detector means for receiving said first outputs and for producing a second output, wherein said second output is representative of a weighted combination of at least two of said first outputs; and
   third detection means operably connected to said second detection means, wherein said third detection means compares said second output against a predetermined criterion determining therefrom if ventricular fibrillation is present.

2. The AED of claim 1, wherein said series of segments are continuous.

3. The AED of claim 1, wherein said at least two of said first outputs are in series.

4. The AED of claim 1, wherein said first detector means is selected from the group consisting of: a complex-domain feed-forward neural network, a complex-domain recurrent neural network, a power spectral density analyzer, a cross-spectral density analyzer, a coherence analyzer, a cepstrum analyzer, and a time-frequency domain analyzer.

5. The AED of claim 1, wherein said second detector means is selected from the group consisting of: a moving average filter, an autoregressive filter, an autoregressive moving average filter, a digitally implemented analog prototyped IIR filter, a Butterworth filter, a type I Chebyshev filter, a type II Chebyshev filter, an elliptic filter, a Bessel filter, a Kalman filter, a multivariate linear predictor, a multivariate nonlinear predictor, and a bayesian predictor.

6. An automatic external defibrillator (AED) having a ventricular fibrillation detector, comprising:
   a first detector portion, wherein said first detector portion receives a cardiac rhythm signal in a series of segments and wherein said first detector portion produces a first output for each of said segments that is representative of either the absence or presence of ventricular fibrillation,
   a second detector portion operably connected to said first detector portion, wherein said second detector portion receives said first outputs and produces a second output, wherein said second output is representative of a weighted combination of at least two of said first outputs; and
   a third detector portion operably connected to said second detector portion, wherein said third detector portion receives said second output and compares said second output against a predetermined criterion determining therefrom if ventricular fibrillation is present.

7. The AED of claim 6, wherein said series of segments are continuous.

8. The AED of claim 6, wherein said at least two of said first outputs are in series.

9. The AED of claim 6, wherein said first detector portion is selected from the group consisting of: a complex-domain feed-forward neural network, a complex-domain recurrent neural network, a power spectral density analyzer, a cross-spectral density analyzer, a coherence analyzer, a cepstrum analyzer, and a time-frequency domain analyzer.

10. The AED of claim 6, wherein said second detector portion is selected from the group consisting of: a moving average filter, an autoregressive filter, an autoregressive moving average filter, a digitally implemented analog prototyped IIR filter, a Butterworth filter, a type I Chebyshev filter, a type II Chebyshev filter, an elliptic filter, a Bessel filter, a Kalman filter, a multivariate linear predictor, a multivariate nonlinear predictor, and a bayesian predictor.

11. An automatic external defibrillator (AED), comprising:
   an electrocardiographic (ECG) system adapted to be connected to a patient for obtaining a cardiac rhythm signal,
   ventricular fibrillation detector operably connected said ECG system, wherein said detector comprises:
      a first detector portion, wherein said first detector portion receives said cardiac rhythm signal in a series of segments and wherein said first detector portion produces a first output for each of said segments that is representative of either the absence or presence of ventricular fibrillation,
      a second detector portion operably connected to said first detector portion, wherein said second detector portion receives said first outputs and produces a second output, wherein said second output is representative of a weighted combination of at least two of said first outputs; and
      a third detector portion operably connected to said second detector portion, wherein said third detector portion receives said second output and compares said second output against a predetermined criterion determining therefrom if ventricular fibrillation, requiring the delivery of a defibrillation pulse, is present; and
   a defibrillation pulse delivery system operably connected to said ventricular fibrillation detector, wherein said defibrillation pulse delivery system delivers said defibrillation pulse upon the determination by said ventricular fibrillation detector that ventricular fibrillation, requiring the delivery of a defibrillation pulse is present.

12. The AED of claim 11, wherein said series of segments are continuous.

13. The AED of claim 11, wherein said at least two of said first outputs are in series.

14. The AED of claim 11, wherein said first detector portion is selected from the group consisting of: a complex-domain feed-forward neural network, a complex-domain recurrent neural network, a power spectral density analyzer, a cross-spectral density analyzer, a coherence analyzer, a cepstrum analyzer, and a time-frequency domain analyzer.

15. The AED of claim 11, wherein said second detector portion is selected from the group consisting of: a moving average filter, an autoregressive filter, an autoregressive moving average filter, a digitally implemented analog prototyped IIR filter, a Butterworth filter, a type I Chebyshev filter, a type II Chebyshev filter, an elliptic filter, a Bessel filter, a Kalman filter, a multivariate linear predictor, a multivariate nonlinear predictor, and a bayesian predictor.

16. In an automatic external defibrillator (AED), a method for detecting ventricular fibrillation, comprising the steps of:
   receiving a cardiac rhythm signal in a series of segments;
   determining the absence or presence of ventricular fibrillation in each of said segments;
   performing a weighted combination of the determinations from at least two of said segments;
   comparing said weighted combination against a predetermined criterion and determining therefrom if ventricular fibrillation is present.

17. The method of claim 16, further comprising the step of initiating the delivery of a defibrillation pulse from the automated external defibrillator if ventricular fibrillation is present.

* * * * *